(12) United States Patent
Lamb

(10) Patent No.: US 7,186,248 B2
(45) Date of Patent: Mar. 6, 2007

(54) DEVICE FOR INTRODUCING AN OBJECT INTO A VAGINA WITH SANITARY FINGER MOUNTING MEANS

(76) Inventor: Peter James Brian Lamb, 12 Clifford Avenue, Irene (ZA) 1675

( * ) Notice: Subject to any disclaimer, the term of this patent is extended or adjusted under 35 U.S.C. 154(b) by 0 days.

(21) Appl. No.: 10/486,841

(22) PCT Filed: Aug. 16, 2002

(86) PCT No.: PCT/IB02/03287

§ 371 (c)(1),
(2), (4) Date: Jun. 22, 2004

(87) PCT Pub. No.: WO03/015680

PCT Pub. Date: Feb. 27, 2003

(65) Prior Publication Data

US 2004/0236265 A1    Nov. 25, 2004

(30) Foreign Application Priority Data

Aug. 16, 2001   (ZA) .................................. 2001/6784

(51) Int. Cl.
*A61F 13/26*  (2006.01)
(52) U.S. Cl. .................... 604/904; 604/11; 604/385.17
(58) Field of Classification Search ............ 604/11–18, 604/904, 385.17; 206/529, 531, 571; 424/430–431; D24/141
See application file for complete search history.

(56) References Cited

U.S. PATENT DOCUMENTS

| | | | | |
|---|---|---|---|---|
| 2,351,836 A | * | 6/1944 | Popper | ........................ 604/16 |
| 3,059,642 A | * | 10/1962 | Gershen | ........................ 604/17 |
| 3,918,452 A | * | 11/1975 | Cornfeld | ...................... 604/515 |
| 4,269,187 A | * | 5/1981 | Sakurai et al. | ................. 604/14 |
| 4,891,042 A | * | 1/1990 | Melvin et al. | ................. 604/18 |
| 5,788,910 A | * | 8/1998 | McNelis et al. | ............ 264/296 |
| 6,186,973 B1 | * | 2/2001 | Buzot | .......................... 604/17 |

FOREIGN PATENT DOCUMENTS

| | | |
|---|---|---|
| DE | 436588 C | 11/1926 |
| EP | 0 064 747 A2 | 11/1982 |
| EP | 0064747 A2 * | 11/1982 |
| FR | 868 718 A | 1/1942 |
| GB | 2 204 495 A | 11/1988 |
| GB | 2204495 A * | 11/1988 |
| GB | 2 227 666 A | 8/1990 |
| GB | 2227666 A * | 8/1990 |
| WO | WO 99/52576 A1 | 10/1999 |

OTHER PUBLICATIONS

The PCT International Search Report dated Apr. 15, 2003 (PCT/IB02/03287).

* cited by examiner

*Primary Examiner*—Tatyana Zalukaeva
*Assistant Examiner*—Laura C Hill
(74) *Attorney, Agent, or Firm*—Woodcock Washburn LLP

(57) ABSTRACT

A device for introducing an object into a vagina includes finger mounting means whereby the device is mountable on a user's finger, and a holder which protrudes from the finger mounting means and which is insertable into a user's vagina, the holder being configured to hold an object whilst being inserted into the user's vagina and then release the object once positioned inside the vagina.

11 Claims, 2 Drawing Sheets

DEVICE FOR INTRODUCING AN OBJECT INTO A VAGINA WITH SANITARY FINGER MOUNTING MEANS

CROSS-REFERENCE TO RELATED APPLICATIONS

This application is a U.S. National Phase of PCT/IB02/03287 filed Aug. 16, 2002, which claims priority to South Africa application number 2001/6784 filed Aug. 16, 2001.

BACKGROUND OF THE INVENTION

THIS INVENTION relates to a device for introducing an object into a vagina.

The inventor is aware of two methods of inserting a tampon into a vagina. In the first method, the user manipulates the tampon by hand and effectively pushes it into her vagina making use of her finger. One disadvantage with this method is that in order to insert the tampon to a sufficient depth, at least a portion of a user's finger must be inserted into the vagina. Naturally, this is unhygienic and undesirable.

The problem is partially overcome by the second method which includes using a paper or plastic applicator comprising an outer tube in which a tampon is mounted and an inner tube which is slidable inside the outer tube and functions as a plunger to displace the tampon from the inner tube once the inner tube has been inserted into the vagina.

However, this method suffers from the disadvantage that the applicator is of a hard and non-pliable material so that there is little or no bend or give during insertion of the device into a vagina. This rigidity makes vaginal insertions more difficult and painful. Often women do not know that the vagina is angled upwards from its opening and that it is not horizontal. After inserting a leading end of the applicator through the vaginal opening in the horizontal direction, the leading end collides with the back wall of the vagina, which is painful and causes the user to think that the applicator has reached the limit of the vagina. The user then deposits the tampon in the vagina at too shallow a depth leading to discomfort.

Further, both methods suffer from the disadvantage that during insertion, a leading end of the tampon is exposed. This results in moisture being absorbed increasing friction between vaginal wall and tampon and so making vaginal insertion more difficult and possibly resulting in malpresentation (incorrect alignment) of the tampon in the vagina. The latter may cause pain or "loss" of the tampon in the vagina.

It is an object of this invention to provide means which the inventor believes will at least alleviate at least some of these problems.

SUMMARY

According to the invention there is provided a device for introducing an object into a vagina which device includes
finger mounting means whereby the device is mountable on a user's finger; and
a holder which protrudes form the finger mounting means and which is insertable into a user's vagina, the holder being configured to hold an object whilst being inserted into the user's vagina and then release the object once positioned inside the vagina.

The inventor believes the device will find application particularly for use in the digital vaginal insertion of tampons. However, the inventor believes the device will be suitable, with or without modification, for the insertion of other objects such as ovuls, suppositories and the like.

The device may include an elongate body, the finger mounting means being in the form of a socket extending longitudinally inwardly from an operatively trailing end of the body within which socket at least an end portion of a user's finger is snugly receivable. A nail receiving recess may lead from the socket. The nail receiving recess serves both the accommodate a user's finger nail and to orientate the device relative to a user's finger.

Naturally, the configuration of the holder will depend on the configuration of the object being inserted.

When the object being inserted is a tampon, the holder may include a cradle within which a tampon is receivable, the cradle being configured such that when a tampon is inserted in the cradle, at least part of the tampon intermediate its ends is exposed.

A leading end of the holder which forms a leading end of the body may be configured to cover a leading end of the tampon. In addition, the leading end of the body may be generally domed to facilitate insertion thereof into a vagina. The leading end of the body may have the general shape or may incorporate at least some of the design features of a glans penis. Thus, the leading end of the body may have a rounded point which flares back like the corona of a glans penis and which in use lifts the opposing vaginal wall when the body is inserted in a vagina by a wedging action.

The leading end of the body, may be split and formed of a flexible material to permit the passage of a tampon therethrough when the device is withdrawn from a user's vagina permitting a tampon to remain in position in the vagina.

The holder may define a seat or recess within which a trailing end of a tampon is receivable.

The socket and the holder may be disposed angularly relative to one another. More particularly, a longitudinal axis of the socket and a longitudinal axis of the holder may be arranged at an obtuse angle relative to one another. The obtuse angle may be between 170° and 135°. Preferably, the obtuse angle is between 160° and 140°, and most preferably between 155° and 145°, and is thus selected to compensate for the angle of vaginal inclination.

The device may include a flexible cover protruding from the trailing end of the body to cover the portion of a user's finger not inserted into the socket and the perineum and the area of the vulva which may come into contact with the user's other fingers.

The socket will typically have a depth which is sufficient to accommodate at least an end portion of a user's finger, typically a middle finger, up to the first phalanx. Hence, the socket will typically have a depth of between 1.5 and 2.5 cm, typically 2 cm. Further, the socket will typically have lateral dimensions of about 1.5 cm.

The holder will typically have a length of between 1.5 and 8 cm, typically 5.5 cm.

The body will typically be formed as a moulding of a synthetic plastics material or polymeric material, such as silicone rubber, or thermoplastic material or paper having a suitable hardness. The desired rigidity of the body at various positions may be achieved by varying the thickness of the body.

BRIEF DESCRIPTION OF THE FIGURES

The invention will now be described, by way of example, with reference to the accompanying diagrammatic drawings.

In the drawings.

DETAILED DESCRIPTION OF EMBODIMENTS

Figure 1:
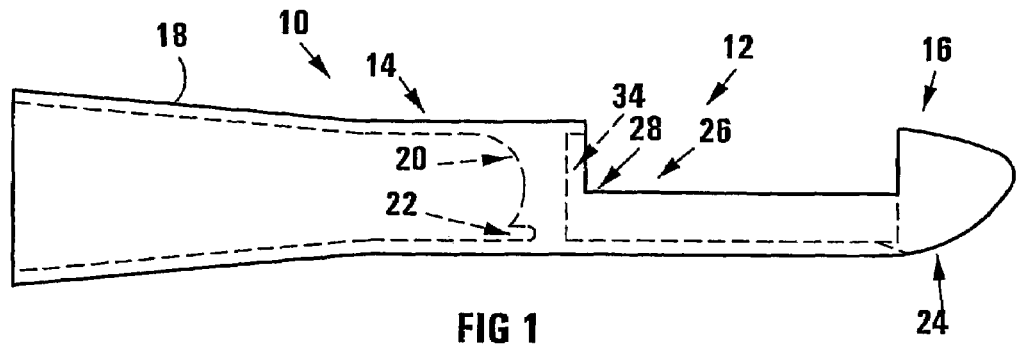
FIG. 1 shows a side view of a device in accordance with the invention.

In FIGS. 1 to 4 of the drawings, reference numeral 10 refers generally to a device for introducing an object into a vagina in accordance with the invention.

The device 10 includes an elongate body 12 having a trailing end 14 and a leading end 16. A flexible cover or skirt 18 protrudes from a trailing end 14 of the body 12.

A socket 20 extends longitudinally inwardly from a trailing end 14 of the body 12. The socket 20 is dimensioned such that an end portion of a user's finger, typically a middle finger, is snugly receivable therein such that the body 12 effectively forms an extension of the user's finger. A nail receiving recess 22 extends from the socket 20 to accommodate a user's finger nail. The nail receiving recess 22 also serves to orientate the body 12 relative to a user's finger as described in more detail herebelow.

A lower part of the body is shaped to be similar to the shape of a lower part of a penis. The leading end 16 of the body 12 generally has the shape of a glans penis. As can best be seen in FIG. 1 of the drawings, a bottom surface 24 of the leading end 16 is curved in side view to inhibit abrasion of the posterior vaginal wall in use. The leading end of the body thus has a rounded point which flares back like the corona of a glans penis which in use lifts and wedges the opposing vaginal walls apart when the body 12 is inserted into a vagina.

The portion of the body 12 extending forwardly from the socket 20 forms a holder in the form of a cradle, generally indicated by reference numeral 26. The cradle 26 defines a circular cylindrical recess 28 within which a tampon 30 is snugly receivable. A longitudinally extending upper portion of the body 12 is open such that a substantial portion of a tampon inserted into the recess 28 is exposed. The cradle 26 defines a seat 34 within which a trailing end portion of the tampon 30 is receivable.

Figure 2:
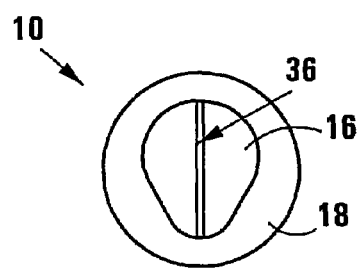
FIG. 2 shows a front view of the device of FIG. 1.

The leading end 16 of the body 12 is split by means of a slit 36 (FIG. 2). The slit permits a tampon to be released from the cradle 26 through the leading end of the body 12 as is described in more detail herebelow.

As can clearly be seen in FIG. 1 of the drawings, the nail receiving recess 22 and the recess 28 are disposed on opposite sides of the body 12 such that, in use, the recess 28 is on that side of the finger corresponding to the inner surface of the finger.

Figure 3:
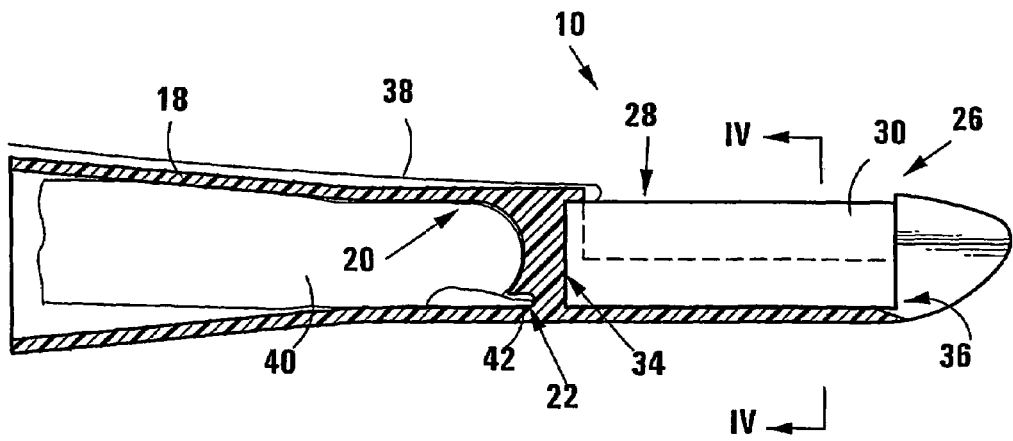
FIG. 3 shows a longitudinal sectional view of the device of FIG. 1.
Figure 4:
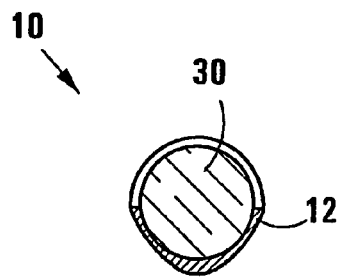
FIG. 4 shows a sectional elevation taken at IV—IV in FIG. 3.

In use, a tampon 30 is positioned in the recess 28 as shown in FIG. 3 of the drawings. A retrieval string 38 attached to a trailing end of the tampon 30 is positioned such that it runs along the outside of the body 12 and cover 18.

A user's finger is inserted into the socket 20 with the finger nail 42 positioned in or in register with the nail receiving recess 22.

Figure 6:
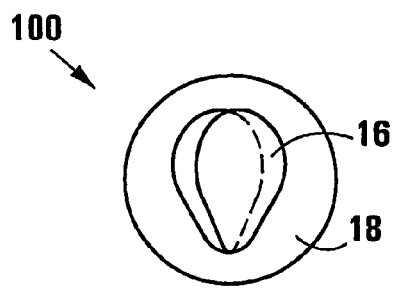
FIG. 6 shows a front view similar to FIG. 2 of another device in accordance with the invention.

The user then inserts the body 12, leading end 16 first, into her vagina. By virtue of the shape of the leading end 16, the two sides of the leading end are urged towards one another as the body 12 is inserted thereby effectively closing the slit 36 and preventing the passage of the tampon 30 therethrough. In another embodiment, shown in FIG. 6, the two sides of a leading end 16 of a device 100 overlap to prevent the passage of a tampon therethrough during insertion of the device 100.

Once the body 12 has been fully inserted, the finger is twisted to dislodge the tampon 28 from the body which is then gently withdrawn from the user's vagina. By virtue of the fact that a substantial portion of the tampon 30 intermediate its ends is exposed, friction between the tampon and the vagina tends to retain the tampon 30 in position. The flexibility of the leading end 16 of the body 12 is selected such that as the body 12 is removed, the two sides of the leading end open up to permit the tampon 30 to pass therethrough and remain in the vagina in the desired position.

The device 10, 100 can then either be washed for re-use or disposed of. In the case of a disposable device 10, 100, it may be pre-packaged with a tampon 30 in position in the recess 28.

Figure 5:
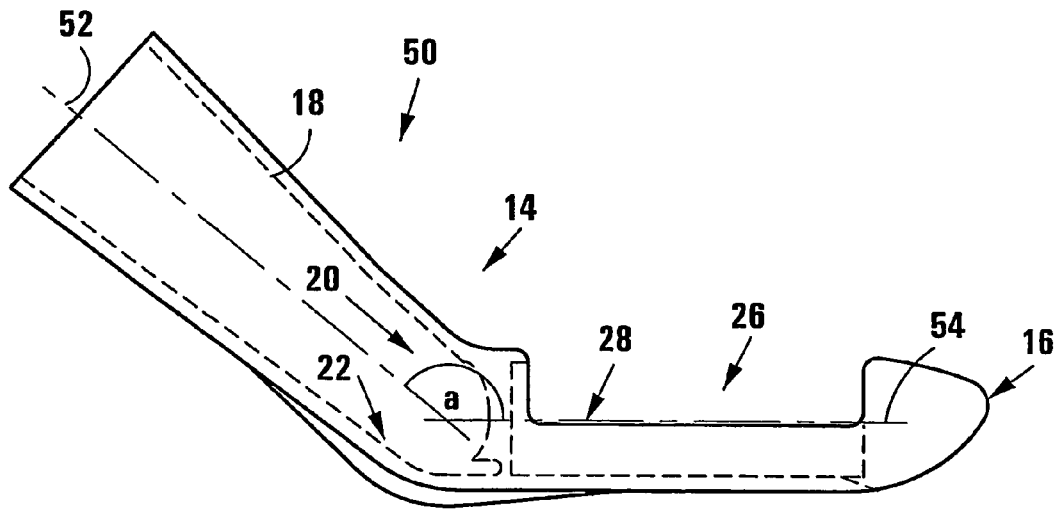
FIG. 5 shows a side view, similar to FIG. 1, of another device in accordance with the invention.

Reference is now made to FIG. 5 of the drawings, in which reference numeral 50 refers generally to another device in accordance with the invention and, unless otherwise indicated, the same reference numerals used above are used to designate similar parts.

The main difference between the device 50, and the device 10 is that, in the case of the device 50, a longitudinal axis 52 of the socket 20 and a longitudinal axis 54 of the cradle 26 are disposed at an angle α relative to one another. The angle is typically about 150°. This corresponds to the angle of inclination of the vagina of a standing woman relative to the horizontal and thereby facilitates correct alignment of the tampon for introduction into the vaginal introitus.

The connection between the part of the body 12 in which the socket 20 is provided and the part of the body 12 defining the cradle is sufficiently flexible to permit the portion of the body 12 in which the socket 20 is provided to be displaced angularly so that the axes 52, 54 can be brought more-or-less into line to facilitate full insertion of the body 12.

This arrangement serves to indicate to the user the correct direction in which the body should be introduced through the introitus and the direction in which the straightened body should be displaced along the vaginal cavity.

The inventor believes that the device 10, 50 includes the following advantages:

The length of the body 12 is not intimidating, but nonetheless provides effective depth of deposition of the tampon or other object into the vagina. The body 12 is of a relatively soft, elastic material which is less difficult and painful to insert than applicators of which the inventor is aware. Further, the cross-section of the body 12 is easier and more comfortable to insert into a vagina. Friction against the back wall of the vagina is reduced due to the shape of the holder.

Further, the glans penis like leading end 16 of the body 12 is easier and more comfortable to insert than the leading end portions of conventional devices. In addition, the shape of the leading end reduces the risk of micro-trauma on the vaginal wall and hence reduces the risk of infection.

In addition, in the device 50, the angle of the socket 20 relative to the holder 26 promotes easier introduction of the holder through the introitus and indicates the direction for its advancement up the vagina. There is a built-in correction for the directional inclination of the vaginal cavity, which causes less risk of injury and discomfort to the user. The holder can be inserted while the user is sitting or standing and the procedure is therefor much easier and more comfortable to accomplish physically and much less an affront to a female's dignity.

In addition, the provision of the cover 18 avoids the user's hand coming into contact with vaginal discharge thereby improving hygiene and reducing the risk of transmission of diseases such as hepatitis and the like. The procedure is more pleasing aesthetically because it avoids contamination of the user's finger and nail by menstrual fluids or vaginal discharge.

The invention claimed is:

1. A device for introducing a tampon into a vagina, said device including:
    an elongate body that is mountable around a user's finger such that the device forms an extension of the user's finger, said elongate body forms a socket therein that extends forward from an operatively trailing end of the body and within the socket at least an end portion of a user's finger is snugly receivable; said socket having a longitudinal axis that is disposed at an obtuse angle relative to a longitudinal axis of a holder; and
    said holder which protrudes forward from the elongate body and which is insertable into a user's vagina, the holder being configured to hold a tampon whilst being inserted into the user's vagina and then release the tampon once positioned inside the vagina, the holder including:
    a cradle defining a circular cylindrical recess within which the tampon is set on top, the cradle being configured such that when the tampon is inserted in the cradle, at least part of the tampon intermediate its outer surface is exposed before insertion, and
    a leading end that is distal relative to the elongate body, the leading end of the holder covering a forward-most tip of the tampon which is distal relative to the elongate body and facing forward during insertion, said leading end of the holder is split and formed of a flexible material to permit the passage of the tampon there through when the device is withdrawn from a user's vagina permitting the tampon to remain in position in the vagina.

2. A device as claimed in claim 1, further comprising a nail receiving recess formed in the socket and within which a nail is receivable, the nail receiving recess leads from the socket towards the holder.

3. A device as claimed in claim 1, in which the leading end of the holder is generally domed to facilitate insertion thereof into a vagina.

4. A device as claimed in claim 1, in which the longitudinal axis of the socket and the longitudinal axis of the holder are arranged at an obtuse angle of between 170° and 135°.

5. A device as claimed in claim 1, in which the device includes a flexible cover protruding from the trailing end of the body to cover the portion of a user's finger not inserted into the socket.

6. A device as claimed in claim 1, in which the leading end of the holder has the general shape or incorporates at least some of the design features of a glans penis.

7. A device for introducing a tampon into a vagina which device includes
    finger mounting means whereby the device is mountable on a user's finger, said finger mounting means includes an elongate body, the finger mounting means being in the form of a socket that extending longitudinally inwardly from an operatively trailing end of the body within which socket at least an end portion of a user's finger is snugly receivable; said socket having a longitudinal axis that is disposed at an obtuse angle relative to a longitudinal axis of a holder; and
    a holder which protrudes forward from the finger mounting means and which is insertable into a user's vagina, the holder being configured to a hold a tampon whilst being inserted into the user's vagina and then release the tampon once positioned inside the vagina, the holder including a cradle defining a circular cylindrical recess within which the tampon is set on top of the cradle; said holder having a leading end that is split and formed of a flexible material to permit the passage of the tampon there through when the device is withdrawn from a user's vagina permitting the tampon to remain in position in the vagina, the cradle being configured such that when the tampon is inserted in the cradle, at least part of the tampon intermediate its outer surface is exposed.

8. A device as claimed in claim 7, in which a nail receiving recess within which a nail is receivable leads from the socket towards the holder.

9. A device as claimed in claim 7, in which a leading end of the holder is configured to cover a leading end of the tampon, the leading end of the body being generally domed to facilitate insertion thereof into a vagina.

10. A device for introducing a tampon into a vagina which device includes
    an elongate body that is mountable on a user's finger; and
    a holder which protrudes forward from the finger mounting means and which is insertable into a user's vagina, the holder being configured to a hold a tampon whilst being inserted into the user's vagina and then release the tampon once positioned inside the vagina, the holder including a cradle defining a circular cylindrical recess within which the tampon is set on top; the holder having a leading end that is split and formed of a flexible material to permit the passage of the tampon there through when the device is withdrawn from a user's vagina permitting the tampon to remain in position in the vagina, said elongate body forms a socket therein that extends forward from an operatively trailing end of the body and within the socket at least an end portion of a users finger is snugly receivable; said socket having a longitudinal axis that is disposed at an obtuse angle relative to a longitudinal axis of a holder; the cradle being configured such that when the tampon is inserted in the cradle, at least part of the tampon intermediate its ends is exposed.

11. The device as claimed in claim 1, wherein the socket is generally finger-shaped.

* * * * *